(12) United States Patent
Vajaria et al.

(10) Patent No.: US 10,997,710 B2
(45) Date of Patent: May 4, 2021

(54) ADAPTIVE CARE AREAS FOR DIE-DIE INSPECTION

(71) Applicant: KLA-TENCOR CORPORATION, Milpitas, CA (US)

(72) Inventors: Himanshu Vajaria, Milpitas, CA (US); Jan Lauber, San Francisco, CA (US); Yong Zhang, Cupertino, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 109 days.

(21) Appl. No.: 16/158,774

(22) Filed: Oct. 12, 2018

(65) Prior Publication Data

US 2019/0114758 A1 Apr. 18, 2019

Related U.S. Application Data

(60) Provisional application No. 62/574,189, filed on Oct. 18, 2017.

(51) Int. Cl.
*G06T 7/00* (2017.01)
*G01N 21/95* (2006.01)
*G01N 21/88* (2006.01)
*G06T 7/11* (2017.01)
*G01N 21/956* (2006.01)

(52) U.S. Cl.
CPC ......... *G06T 7/001* (2013.01); *G01N 21/8851* (2013.01); *G01N 21/9501* (2013.01); *G01N 21/95607* (2013.01); *G06T 7/11* (2017.01); *G01N 2021/95615* (2013.01); *G06T 2207/20104* (2013.01); *G06T 2207/30148* (2013.01)

(58) Field of Classification Search
CPC . G06T 7/001; G06T 7/11; G06T 2207/20104; G06T 2207/30148; G01N 21/9501; G01N 21/8851; G01N 21/95607; G01N 2021/95615
USPC ....................................................... 382/149
See application file for complete search history.

(56) References Cited

U.S. PATENT DOCUMENTS

| 9,255,787 B1 | 2/2016 | Manassen et al. |
| 2010/0246931 A1* | 9/2010 | Kim ..................... G01N 21/956 382/141 |
| 2014/0376802 A1* | 12/2014 | Wu ........................ G06T 7/001 382/149 |

FOREIGN PATENT DOCUMENTS

| JP | H05150442 A | 6/1993 |
| JP | 2017129369 A | 7/2017 |

OTHER PUBLICATIONS

ISA/KR, International Search Report and Written Opinion for PCT/US2018/056209 dated Feb. 7, 2019.

* cited by examiner

*Primary Examiner* — Amandeep Saini
(74) *Attorney, Agent, or Firm* — Hodgson Russ LLP

(57) ABSTRACT

The present disclosure describes methods, systems, and articles of manufacture for performing a defect inspection of a die image using adaptive care areas (ACAs). The use of ACAs solve the problem of handling rotations of components that require rotating care areas; handling the situation where each care area requires its own rotation, translation, or affine transformation; and the situation of decoupling intensity differences caused by defects or process variation from intensity differences caused by size variations.

20 Claims, 13 Drawing Sheets

ADAPTIVE CARE AREAS FOR DIE-DIE INSPECTION

CROSS REFERENCE TO RELATED APPLICATIONS

This application claims priority to U.S. Provisional Application No. 62/574,189, filed on Oct. 18, 2017, the disclosure of which is hereby incorporated by reference.

FIELD OF THE DISCLOSURE

The disclosure generally relates to identifying defects in semiconductor devices.

BACKGROUND OF THE DISCLOSURE

Evolution of the semiconductor manufacturing industry is placing greater demands on yield management and, in particular, on metrology and inspection systems. Critical dimensions continue to shrink, yet the industry needs to decrease time for achieving high-yield, high-value production. Minimizing the total time from detecting a yield problem to fixing it determines the return-on-investment for a semiconductor manufacturer.

Fabricating semiconductor devices, such as logic and memory devices, typically includes processing a semiconductor wafer using a large number of fabrication processes to form various features and multiple levels of the semiconductor devices. For example, lithography is a semiconductor fabrication process that involves transferring a pattern from a reticle to a photoresist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during semiconductor manufacturing to detect defects on wafers to promote higher yield in the manufacturing process and, thus, higher profits. Inspection has always been an important part of fabricating semiconductor devices such as integrated circuits (ICs). However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary because even relatively small defects may cause unwanted aberrations in the semiconductor devices.

In some semiconductor inspection recipes, users draw care areas, which are rectangles defined by their width, height, and x and y offset from a fixed origin such as the die corner. The care areas are defined at setup time using a single wafer. During inspection, these care areas are placed with respect to the die corners for each wafer to be inspected thereafter. Under certain conditions, this approach is sufficiently accurate for inspection. However, there are several use cases where this approach lacks accuracy and is insufficient. For example, aligning the dies and shifting the care areas can negatively affect accuracy.

If there are multiple dies that composite a single die (e.g., reconstituted dies) then each constituent die will vary in placement with respect to the die corner. This prevents the care areas from being offset by a common shift. Thus, each care area needs to have its own adjustment, which can include shift and rotation.

Previous approaches cannot account for changes in size of the underlying feature. For example, if the bond pads in a current wafer are of a different size than the wafer on which care areas were drawn, parts of the bond pad may go uninspected or may cause nuisance defects.

Previous approaches also cannot account for when multiple layers are visible and there are care areas around structures in each layer. The individual layers may have some shift due to the stepper, and so a global alignment will not be able to shift care areas properly.

FIGS. 1-4 provide examples and additional explanation of the problems solved by the present disclosure.

FIG. 1 illustrates an example of a die image 100. Within die image 100 are square features 101, redistribution layer (RDL) 102, and pillar features 103. Die image 100 is an example of a die with features in ideal alignment and ideal scale. This ideal alignment and ideal scale is discernable when a care area is overlaid on the die image.

FIG. 2 illustrates an example of the placement of care areas on a die image 200. A plurality of care areas have been overlaid (dotted lines) on features including square features 201 with square care area regions overlaid, RDL features 202 with rectangle care area regions overlaid, and pillar features 203 with circle care area regions overlaid. In FIG. 2, the depicted care areas are in alignment with and are properly scaled to the features 201, 202, and 203 on the die image 200.

FIG. 3 illustrates an example of a die image 300. Within die image 300 are square features 301, RDL features 302, and pillar features 303. Die image 300 is an example of a die with features in non-ideal alignment or non-ideal scale in accordance with some of the use cases discussed herein. This non-ideal alignment or non-ideal scaling is discernable when a care area is overlaid on the die image.

FIG. 4 illustrates an example of the placement of care areas on a die image 400. A plurality of care areas have been overlaid (dotted lines) on features including square features 401 with square care area regions overlaid, RDL features 402 with rectangle care area regions overlaid, and pillar features 403 with circle care area regions overlaid. In FIG. 4, the depicted care areas are out-of-alignment with and improperly scaled to the features 401, 402, and 403 on the die image 400.

In summary, the previous methods do not address the core problem of a spatial shift of the underlying structure.

Therefore, improved defect identification methods and systems are needed.

SUMMARY OF THE DISCLOSURE

An embodiment of the present disclosure is a method of performing a defect inspection comprising defining at least one adaptive care area. The adaptive care area has a plurality of pre-determined properties comprising an x-coordinate; a y-coordinate; and a shape. The adaptive care area is saved to a recipe that is stored within an electronic data storage unit. A die image of a wafer on a stage is obtained using an inspection tool comprising a particle emitter and a detector. At a processor, the recipe is read from the electronic data storage unit. The processor is used for the adaptive care area saved in the recipe by determining a first location on the die image corresponding to the adaptive care area; overlaying the adaptive care area on the first location on the die image; adjusting the adaptive care area to one or more corresponding features on the die image; and performing a defect inspection of the die image within the adaptive care area.

The particle emitter can include a broadband plasma source, electron beam source, lamp, or laser. The particle emitter can emit electrons or photons. In some embodiments, the particle emitter can also emit light, which can be infrared, visible, ultraviolet, or x-ray light.

The shape can be a polygon, an ellipse, or any user-defined irregular shape. The plurality of pre-determined properties can further comprise at least one feature property, which can be a scaled invariant feature transform, a speeded-up robust feature, an oriented rotated brief, a histogram of oriented gradients, a corner-detector, or a gradient-based descriptor. The shape can be any polygon, and adjusting the adaptive care area can comprise adjusting at least one corner of the polygon. Adjustment of the corner of the polygon can be constrained by one or more adjustment limits.

In an instance, adjusting the adaptive care area to one or more corresponding features on the die image can be one or more of translation, rotation, scaling, affine transformation, perspective warping, or projective distortion. Adjusting the adaptive care area can further involve determining one or more adjustment limits and constraining the adjustment of the adaptive care area by the one or more adjustment limits.

One embodiment of the present disclosure involves performing a preliminary adjustment to an adaptive care area prior to using the inspection tool to obtain the die image. The preliminary adjustment to the adaptive care area can comprise obtaining a reference die image of a reference die, and at the processor, reading the recipe from the electronic data storage unit. The processor can be used for the adaptive care area saved in the recipe by: determining a second location on the reference die image corresponding to the adaptive care area, overlaying the adaptive care area on the second location on the reference die image, and preliminarily adjusting the adaptive care area to one or more corresponding elements on the reference die image. The reference die can be a golden die having verified features, a synthetic die calculated from the median of neighboring dies, or a design image simulated from a design file In another embodiment of the present disclosure, a defect inspection system comprises an inspection tool, an electronic data storage medium, and a processor in electronic communication with the inspection tool and the electronic data storage unit. The inspection tool further comprises a particle emitter configured to emit particles in a particle beam, a stage configured to hold a wafer in a path of the particle beam emitted by the particle emitter, and a detector configured to detect a portion of the particles reflected by the wafer and yield a die image. The electronic data storage medium is configured to store a recipe that includes at least one adaptive care area. The adaptive care area has a plurality of pre-determined properties comprising an x-coordinate, a y-coordinate, and a shape. The processor is configured to receive the die image from the inspection tool; read the recipe from the electronic data storage unit, and for each adaptive care area saved in the recipe: determine a first location on the die image corresponding to the adaptive care area, overlay the adaptive care area on the first location on the die image; adjust the adaptive care area to one or more corresponding elements on the die image; and perform a defect inspection of the die image within the adaptive care area.

The processor of a system according to an embodiment of the present disclosure can be further configured to read the recipe from the electronic data storage unit. For the adaptive care area saved in the recipe, the processor may determine a second location on a reference die image corresponding to the adaptive care area; overlay the adaptive care area on the second location on the reference die image; and preliminarily adjust the adaptive care area to one or more corresponding features on the reference die image. The reference die image may be obtained from a golden die having verified features, a synthetic die calculated from the median of neighboring dies, or a design image simulated from a design file.

The particles emitted from the particle emitter can be photons or electrons. In some embodiments, the particle emitter can also emit light, which can be infrared, visible, ultraviolet, or x-ray light.

The shape pre-determined property of the adaptive care area can be a polygon, ellipse, or a user-defined irregular shape.

Another embodiment of the present disclosure can be a non-transitory computer-readable storage medium, comprising one or more programs. The one or more programs can execute the following steps on one or more computing devices. An adaptive care area is defined. The adaptive care area has a plurality of pre-determined properties comprising: an x-coordinate; a y-coordinate; and a shape. The adaptive care area is saved to a recipe. A die image of a wafer on a stage is obtained from an inspection tool comprising a particle emitter and a detector. The recipe is read. For each adaptive care area saved in the recipe, a location on the die image corresponding to the adaptive care area is determined. The adaptive care area is overlaid on the location on the die image. The adaptive care area is adjusted to one or more corresponding features on the die image. Instructions to perform a defect inspection of the die image within the adaptive care area are sent.

The non-transitory computer-readable storage medium can comprise a program further configured to define an adaptive care area having a plurality of pre-determined properties, including a shape, wherein the shape is either a polygon, ellipse, or other user-defined irregular shape.

The non-transitory computer-readable storage medium can comprise a program further configured to implement one or more adjustment limits that are determined, wherein adjusting the adaptive care area to one or more corresponding features in the die image is constrained by the one or more adjustment limits.

BRIEF DESCRIPTION OF THE FIGURES

For a fuller understanding of the nature and objects of the disclosure, reference should be made to the following detailed description taken in conjunction with the accompanying drawings, in which.

DETAILED DESCRIPTION OF THE DISCLOSURE

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

This disclosure describes a new method of defining and using Adaptive Care Areas (hereinafter ACAs) for inspection of a die image. Embodiments disclosed herein modify the care areas dynamically, as compared to previous methods of aligning the underlying images. Embodiments disclosed herein describe methods, systems, and articles of manufacture containing software for performing a defect inspection of a die image. The ACAs described in the present disclosure solve the problems of previous techniques. Thus, the disclosed techniques can handle rotations of components that may require rotating the care areas. The disclosed techniques also can handle a situation when each care area gets its own rotation, translation, and possibly affine transformation. This can decouple intensity differences caused by defects or process variation from intensity differences caused by size variations due to the ACA fitting the feature to be inspected with greater precision. Using the former methods, false defect reports arose due to intensity readings from imprecisely fit care areas.

Figure 11:
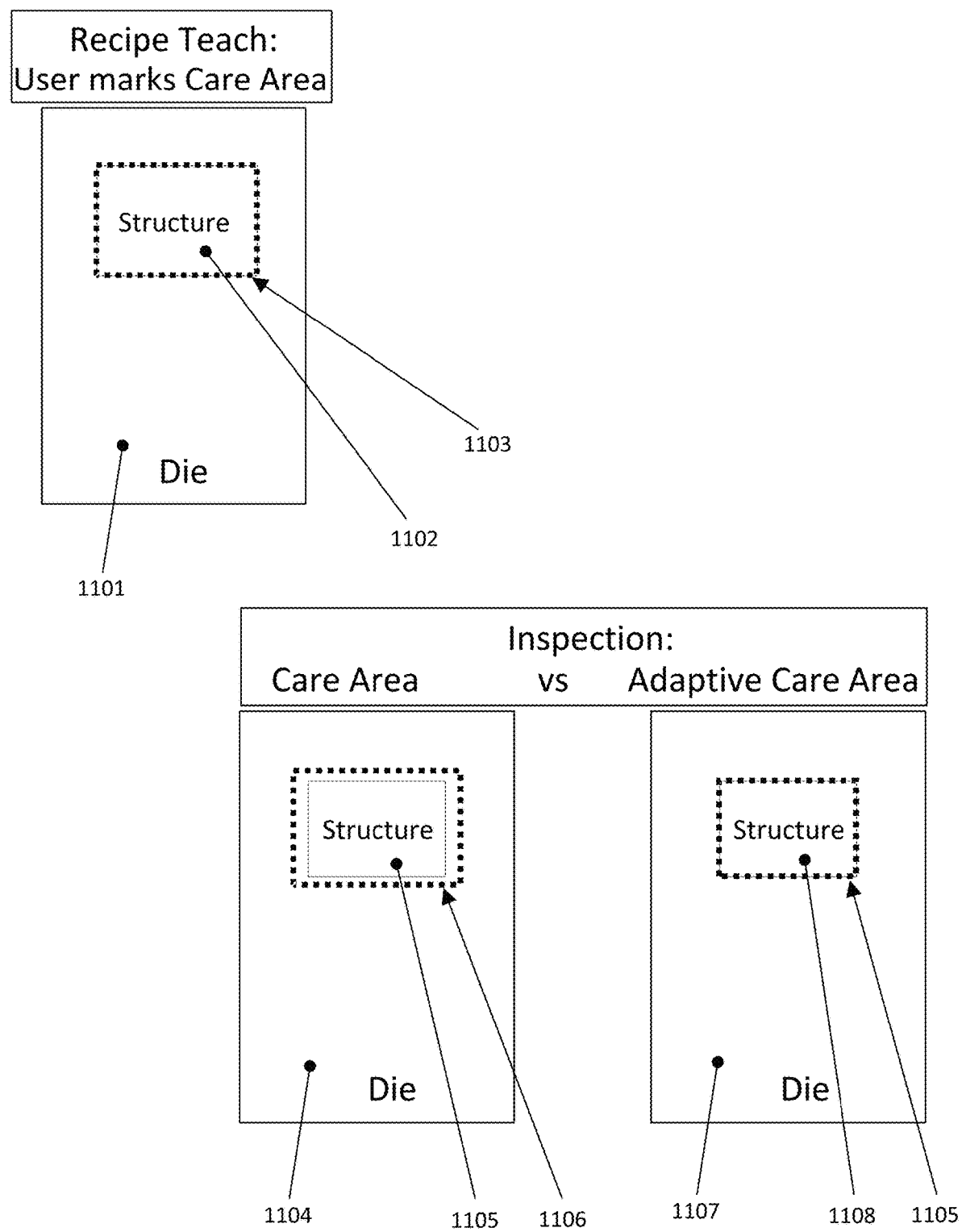
FIG. 11 illustrates a comparison of defect reporting due to a care area with an adaptive care area in an embodiment of the present disclosure.

FIG. 11 illustrates the effects on defect reporting due to an imprecisely fit care area as compared to an ACA's precise fit in an embodiment of the present disclosure. For instance, a care area 1103 is defined for a feature 1102 on a die 1101 and stored in a recipe. When this recipe is used in an inspection of die 1104 using former methods, a feature 1105 can be undersized, causing the care area 1106 to align, but be imprecisely fit as the size and shape of the care area is not changed. This imprecise fit can lead to inaccurate intensity readings that can lead to reporting a false defect, even though the feature was within permissible size variation ranges. However, according to an embodiment of the present disclosure, the care area can be an ACA 1105, which adapts (or "snaps") to the undersized feature 1108 on die 1107. This allows reporting of the fact that adapting occurred, which allows an inspection to differentiate between intensity differences caused by defects or process variation from intensity differences caused by size variations. In this way, embodiments of the present disclosure have greater accuracy than traditional methods of alignment.

The methods, systems, and articles of manufacture disclosed herein can handle situations when feature sizes on a die are different, when features have undergone rotations, when offsets of features are arbitrarily large, and/or when different structures in the job frame have undergone different offsets. Further, the present disclosure can decouple placement errors, size errors, and structural defects, which were previously all bundled into a single error.

Embodiments of the present disclosure are faster than traditional image alignment methods. Additionally, embodiments of the present disclosure utilize fewer computational resources than previous methods of alignment. For instance, in traditional alignment methods such as template-based image alignment, all pixels in the image are taken into account, yielding a computational complexity of $O(n^2)$, where n is the image dimension in pixels. If a search window for the pixel is m, the search must be done m times, meaning that it would take $m^2 * n^2$ operations to find the match. Where salient point alignments are made for an ACA according to an embodiment of the present disclosure, there are k alignments that can be done, requiring $m^2 * k$ operations to form the match. Thus, an embodiment of the present disclosure can require $m^2/k$ times fewer operations, yielding increased computational efficiency of feature matching.

Embodiments of the present disclosure address the problems of feature misalignment directly rather than relying only on alignment of the die to mask the issue. The present disclosure can address arbitrary shifts, rotations, and spatial deformations. It can be used with care areas that are rectangles, general polygons, conics, and non-parametric shapes. It also can address the case where there are multiple layers with different shifts in a die image.

Figure 1:
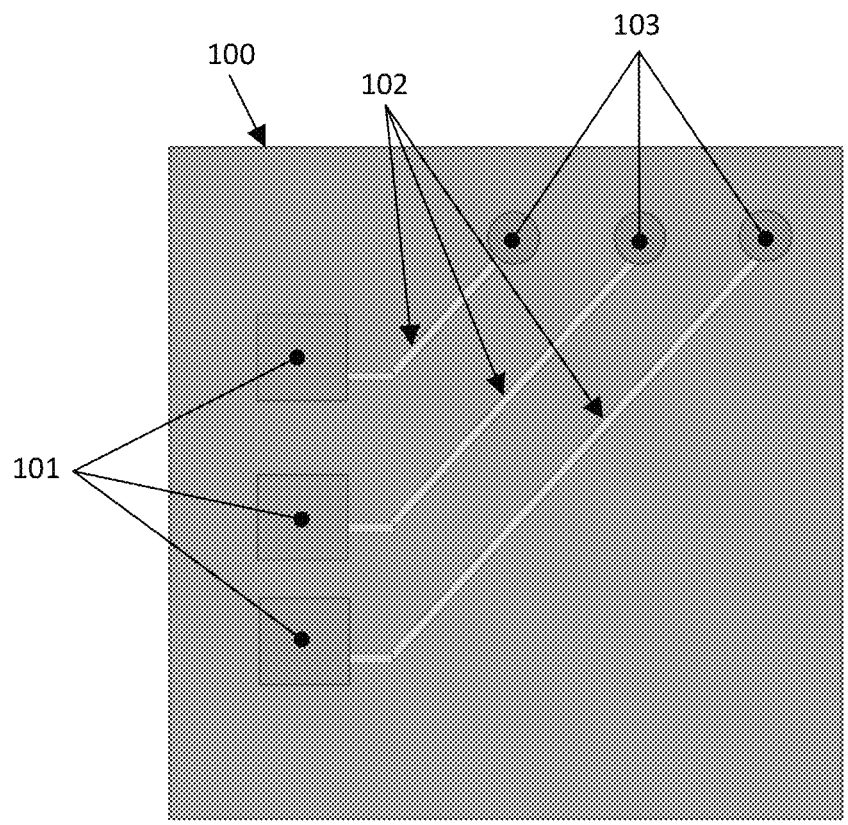
FIG. 1 illustrates a section of a die image wherein a plurality of features are in ideal alignment and ideal scale.
Figure 2:
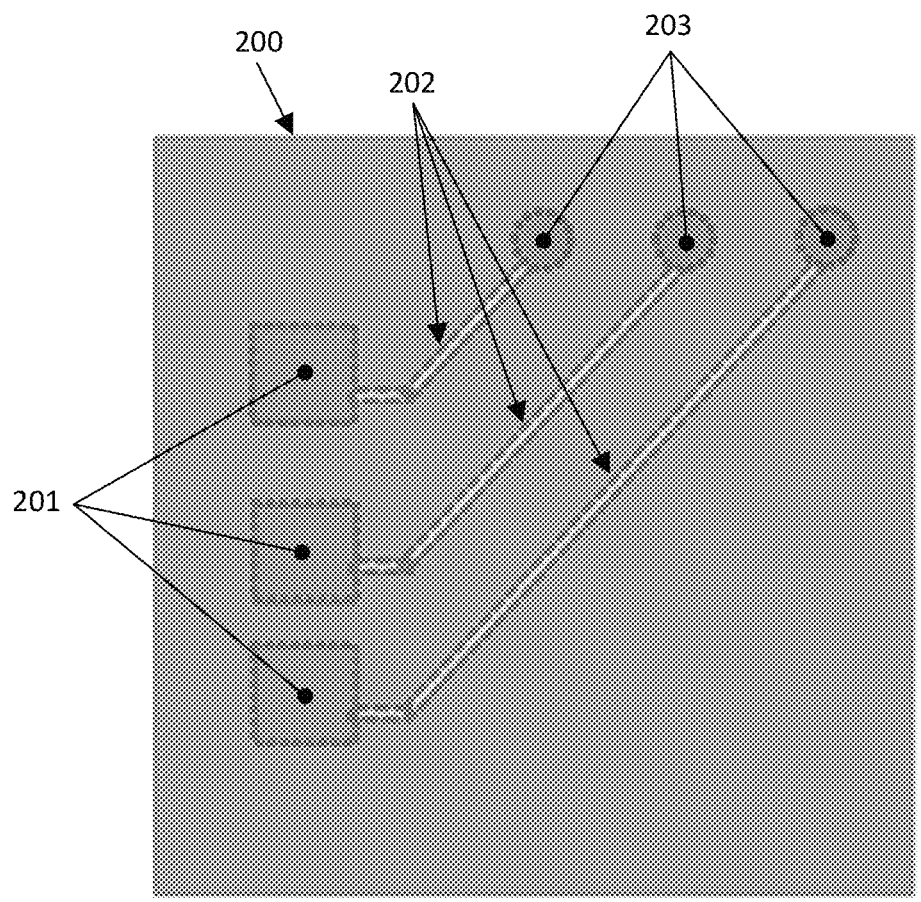
FIG. 2 illustrates the placement of care areas on a die image wherein a plurality of features are in ideal alignment and ideal scale.
Figure 3:
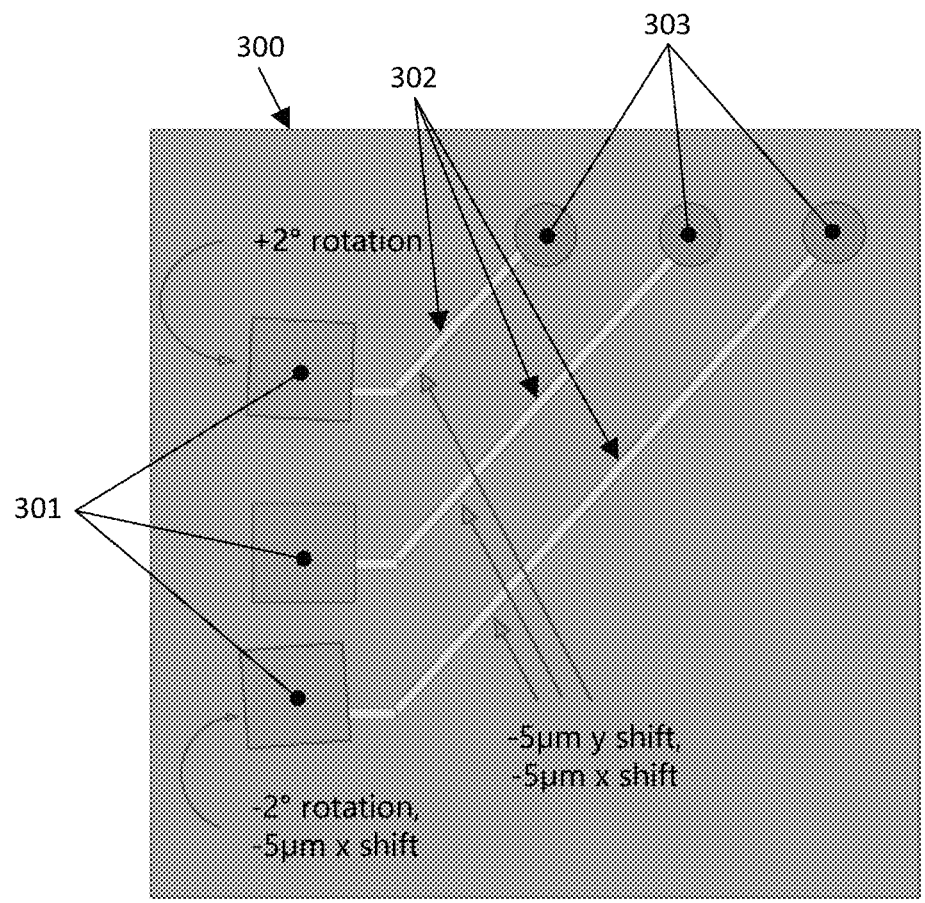
FIG. 3 illustrates a section of a die image wherein a plurality of features are in non-ideal alignment or non-ideal scale.
Figure 4:
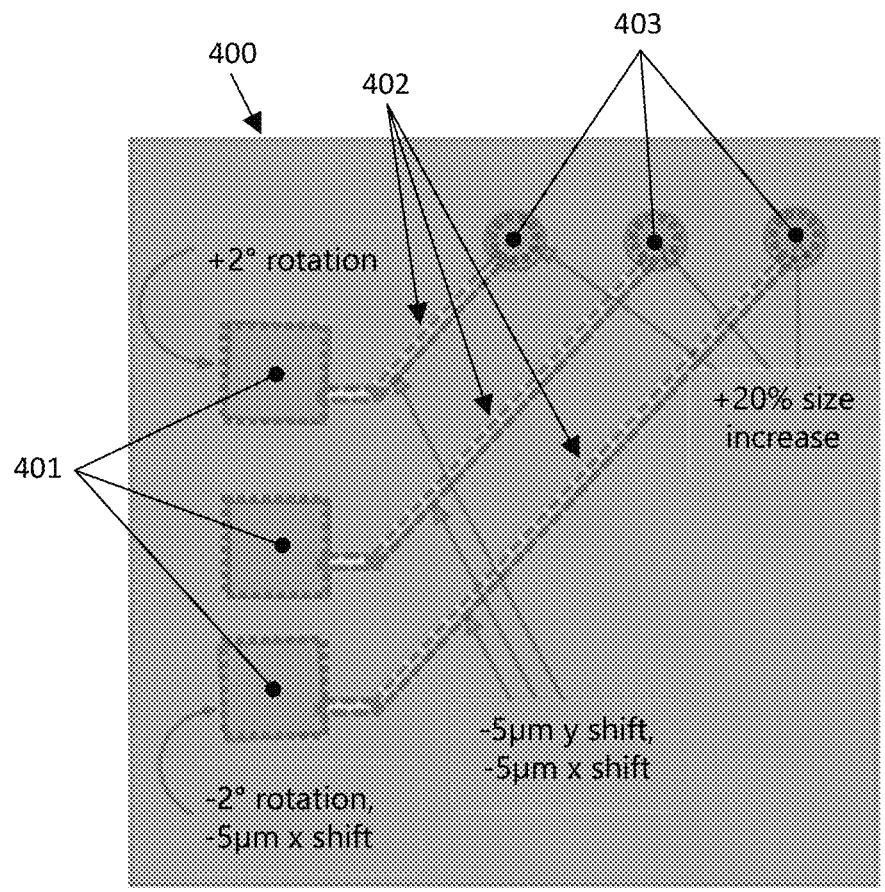
FIG. 4 illustrates the placement of care areas on a die image wherein a plurality of features are in non-ideal alignment or non-ideal scale.
Figure 5:
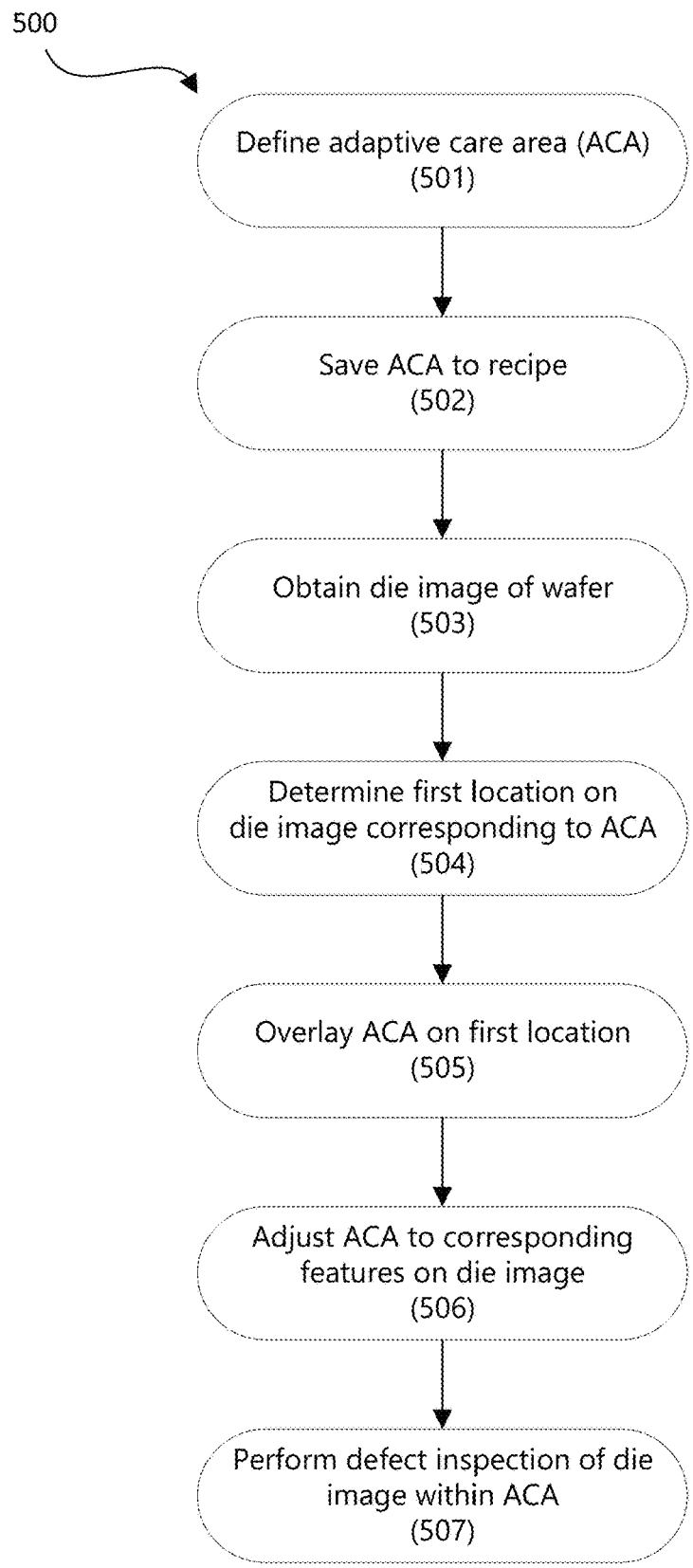
FIG. 5 illustrates a method of performing a defect inspection in accordance with the present disclosure.

FIG. 5 depicts an embodiment of the present disclosure in method 500 of performing a defect inspection of a die image or other file. The method 500 comprises defining an ACA 501, saving the ACA to a recipe 502, obtaining a die image of a wafer 503, determining a first location on the die image corresponding to the ACA 504, overlaying the ACA on the first location 505, adjusting the ACA to corresponding features on the die image 506, and performing a defect inspection 507 of the die image within the ACA. The defect inspection 507 can involve finding defects within the ACA.

The first location may be determined based on salient points defined with the ACA. In this instance, each of the salient points within the ACA corresponds to a location and featured descriptor, which are stored in the recipe. Then, for determining the first location, for each salient point, feature descriptors are extracted within all points in a radius of that salient point. Then, these are matched to feature descriptors in the recipe, and the new location of the salient point is the one for which the maximum is maximized. In some instances, sub-pixel location estimation is then performed to more finely align to the first location.

Figure 12:
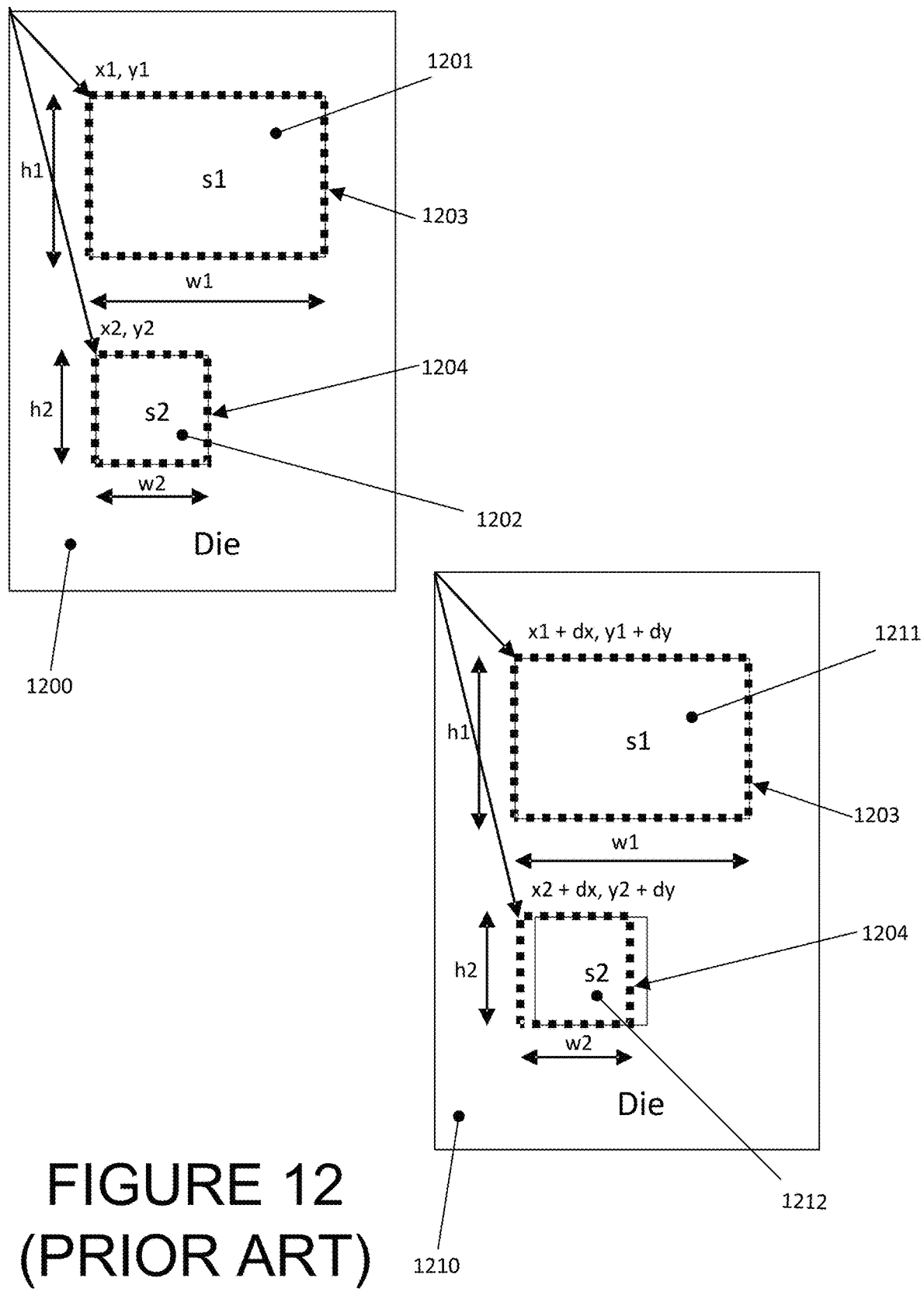
FIG. 12 illustrates a care area alignment where the care area is misaligned.

In order to differentiate embodiments of the present disclosure from the previous methods, a former method is described. In an instance, care areas may be defined and overlaid as illustrated in FIG. 12. According to some previous methods, on a teach die 1200, first care area 1203 may be defined based on feature 1201 by a height h1, a width w1, and a position (x1, y1) fixed relative to an origin. Also on teach die 1200, a second care area 1204 may be defined based on a feature 1202 by a height h2, a width w2, and a position (x2, y2) fixed relative to the same origin. The first and second ACAs may be stored to a recipe. During an inspection, this recipe is used. Care areas 1203 and 1204 are overlaid on features 1211 and 1212, respectively on die 1210. The positions of the care areas 1203 and 1204 can be shifted by an origin shift (dx, dy); the same offset is used to adjust the position of each care areas, thus permitting only global shifts. This is problematic where individual features are offset relative to each other, as illustrated on die 1210, as it results in sub-optimal shifts applied to some or all of the structures. As illustrated on die 1210, the origin shift (dx, dy) results in a fit of care area 1203 to feature 1211, but a sub-optimal offset of care area 1204 in relation to feature 1212, as the same origin shift must be applied to every care area in this method.

Figure 13:
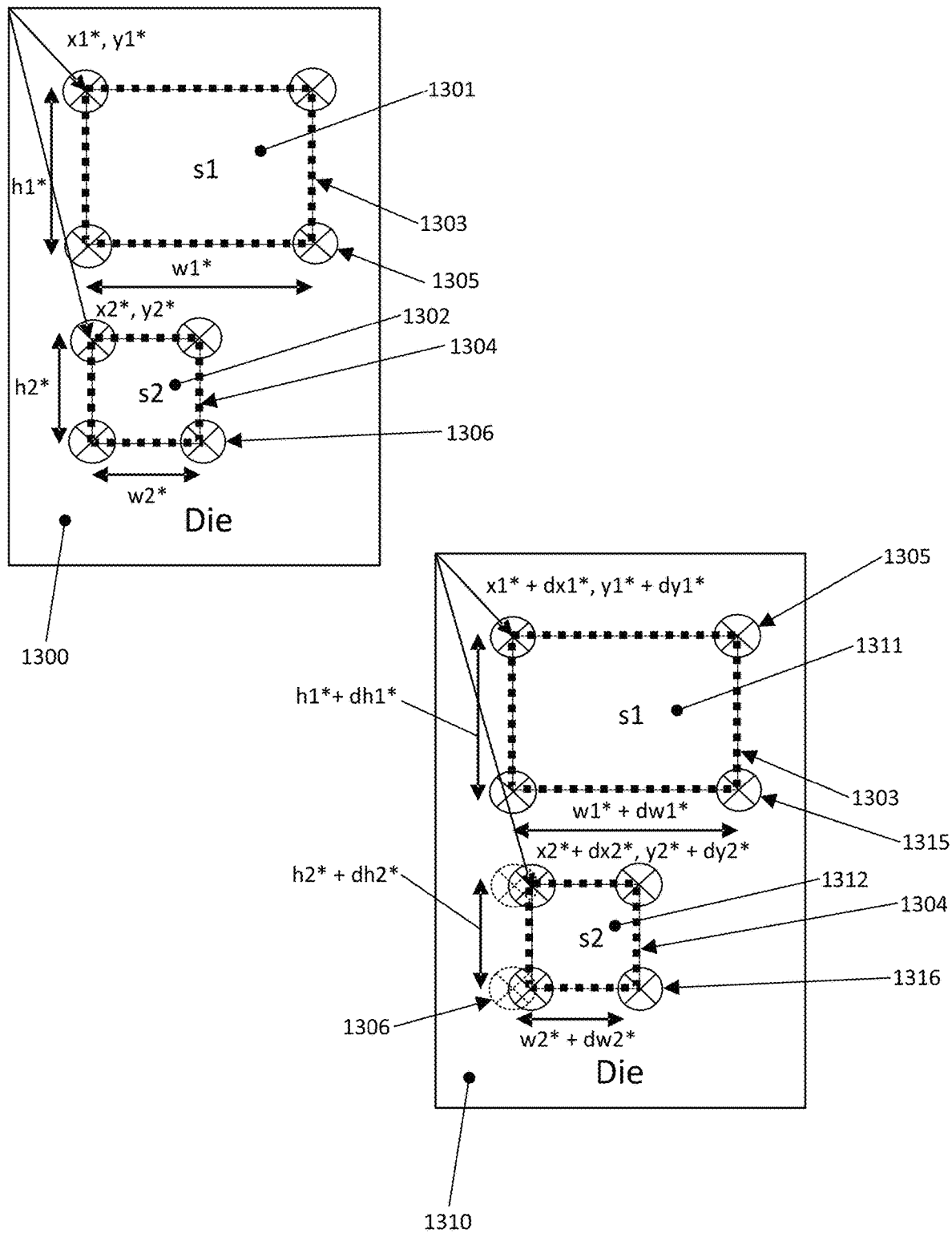
FIG. 13 illustrates ACA alignment according to an embodiment of the present disclosure.

In contrast and according to an embodiment of the present disclosure, on a teach die 1300 of FIG. 13, first ACA 1303 may be defined based on feature 1301 by a height $h1^*$, a width $w1^*$, and a position $(x1^*, y1^*)$, and having salient points 1305. Also on teach die 1300, a second ACA 1304 may be defined based on a feature 1302 by a height $h2^*$, a width $w2^*$, and a position $(x2^*, y2^*)$, and having salient points 1306. Each salient points given, for example, by 1305 and 1306 have a unique feature descriptor, such as simple gradients or richer speeded-up robust feature (SURF)-like features. Such features can include, but are not limited to Binary Feature Detectors such as scaled invariant feature transform (SIFT), SURF, oriented rotated brief (ORB), and histogram of oriented gradients (HOG), as well as corner-detectors and gradient-based image descriptors. The first and second ACAs may be stored to a recipe with their respective feature descriptors containing, inter alia, their relevant dimensions, coordinates, and salient points. At inspection time, the ACAs 1303 and 1304 are overlaid on die 1310. A search is performed to detect the salient points based on the feature descriptor for ACA 1303 stored in the recipe. Based on the search results, ACA 1303 is modified to have a height $h1^*+dh1^*$, a width $w1^*+dw1^*$, and a position $(x1^*+dx1^*, y1^*+dy1^*)$, so that it now adapts to the current feature 1311. Each salient point 1305 can be allowed to move independently, allowing ACA 1303 to have translation, rotation, and general projective transforms so that it accurately fits feature 1311's actual salient points 1315. Similarly, a search is performed to detect the salient points based on the feature descriptor for ACA 1304 stored in the recipe. Based on the search results, ACA 1304 is modified to have a height $h2^*+dh2^*$, a width $w2^*+dw2^*$, and a position $(x2^*+dx2^*, y2^*+dy2^*)$, so that it now adapts to the current feature 1312. Each salient point 1306 can be allowed to move independently, allowing ACA 1304 to have translation, rotation, and general projective transforms so that it accurately fits feature 1312's actual salient points 1316. In this way, each ACA can have an independent position origin shift. This allows the ACA to properly fit the actual structures even if they undergo independent translation, rotation, or even any projective transformation relative to each other. It leads to robust defect detection and further disambiguates intensity differences from size/shape differences.

Adjusting the ACA to one or more corresponding features on the die image can include one or more of translation, rotation, scaling, affine transformation, perspective warping, or projective distortion.

Turning back to FIG. 5, in some embodiments of the present disclosure, there may be one or more ACAs defined at 501, saved to a recipe at 502, and fitted and used for inspection in 503-507.

Referring to FIG. 5, in an embodiment of the present disclosure, each ACA is defined by a shape or set of shapes. At runtime, ACAs are initially placed at locations defined during setup. Then, the ACAs adjust to match the features on the inspected wafer. For example, each corner, center point, or inflection point can try to match its feature set. This allows for the ACA to be flexible in terms of its dimensions and rotation.

During the defect reporting phase of the inspection process, the amount of rotation, translation, scaling, or other transformation can be added as an attribute that decouples placement or sizing errors from structural errors. This can include, after the ACA has adjusted to its corresponding features, reporting a degree of adjustment using appropriate attributes that capture the magnitude of translation and rotation, as well as other parameters that can quantify the scaling, affine, or projective distortion. This yields shape-deformation based attributes of a defect, beyond the previously discoverable intensity-based attributes. The decoupling can provide for a better analysis of the defects.

The permissible movement of each corner, center point, or inflection point may be constrained by deformation limit, which defines an allowable amount of deformation of the shape defined. The deformation limit can also be a limit on the permissible types of transformations. For instance, deformation can be limited to one or multiple transformations from a list including: translation, rotation, scaling, affine, and projective transformation. A deformation could also be limited to permissible shapes to which an ACA can deform.

In an embodiment of the present disclosure, during inspection of a die image, the regions within the ACA may undergo affine or perspective warping to allow for pixel-wise subtraction. Alternatively, the regions can be used as-is for purposes of computing statistics.

In an instance, at inspection time, transformation can be applied to a feature on a die for feature matching purposes and intensity determination purposes.

In an embodiment of the present disclosure, defining one or more ACAs is comprised of converting one or more care areas into ACAs.

In an embodiment of the present disclosure, ACAs are defined by a user, who draws care areas on a die image. These can be drawn as shapes such as, inter alia, rectangles, circles, parallelograms, or any arbitrary polygon (convex and non-convex), or could be any free drawn shape. The user can select features to be found, for instance, corners, edges, or circles, or other features. The user can select a method to use for detecting the features, and select a feature descriptor. The user can also select the kinds and range of allowed deformations. The ACA features from which a user may select may be initialized to defaults, but the user can refine the automated choices.

Each of the shapes or set of shapes that define the ACAs can be defined as a polygon, ellipse, circle, or any other irregular or free-drawn shape with or without curve smoothing. Free-drawn shapes can remain free-drawn shapes, with salient points added, or be converted to polygons. The shapes may be encoded by their spatial properties and also features of their salient points or edges. The spatial properties can include, for example, corners, focus-radii, side lengths, or other properties. Features of the shapes can be simple gradients or richer SURF-like features. Such features can include, but are not limited to Binary Feature Detectors such as SIFT, SURF, ORB, and HOG, as well as corner-detectors and gradient-based image descriptors. Similarly, edge features can be gradients, projection sums on each side of an edge, or other richer features computed in the neighborhood of an edge, curve, or corner.

Each of the shapes or set of shapes that define the ACAs can also be three-dimensional shapes, such as, inter alia, parallelepipeds, prisms, pyramids, and cylinders, rather than two-dimensional primitives. These three-dimensional shapes can be converted automatically from two-dimensional primitives based on user-defined parameters.

In some embodiments, the salient points are detected automatically upon the definition or drawing of an ACA.

In an embodiment of the present disclosure, the shape of an ACA is a rectangle defined by its x and y position on the die, and its width, height, and features computed from the corners and edges. This rectangle can then deform into, inter alia, an arbitrary quadrilateral, parallelogram, trapezoid, or rectangle as may be necessitated by the use case. This deformation may be constrained by a deformation limit, which may be determined by a user as a parameter of an ACA.

In an embodiment of the present disclosure, an ACA is originally defined non-parametrically, and parametrized by computing salient points along its contour, coupled with computation of features in its neighborhood.

Figure 6:
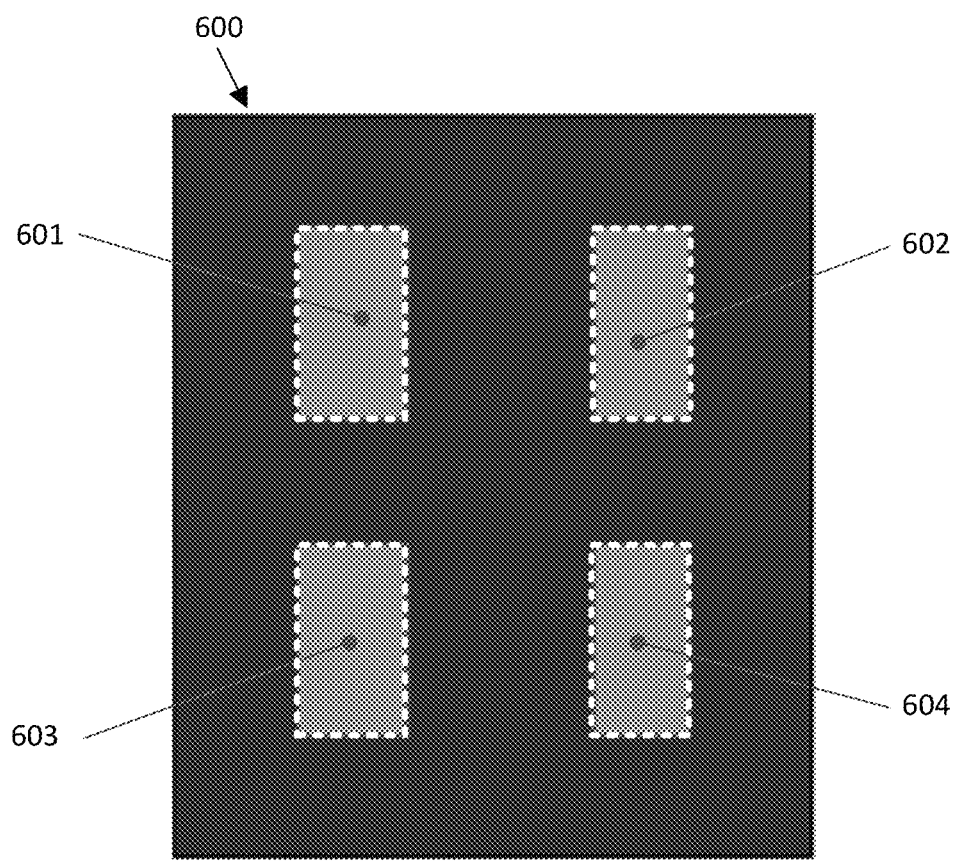
FIG. 6 illustrates care areas as drawn on a die.
Figure 7:
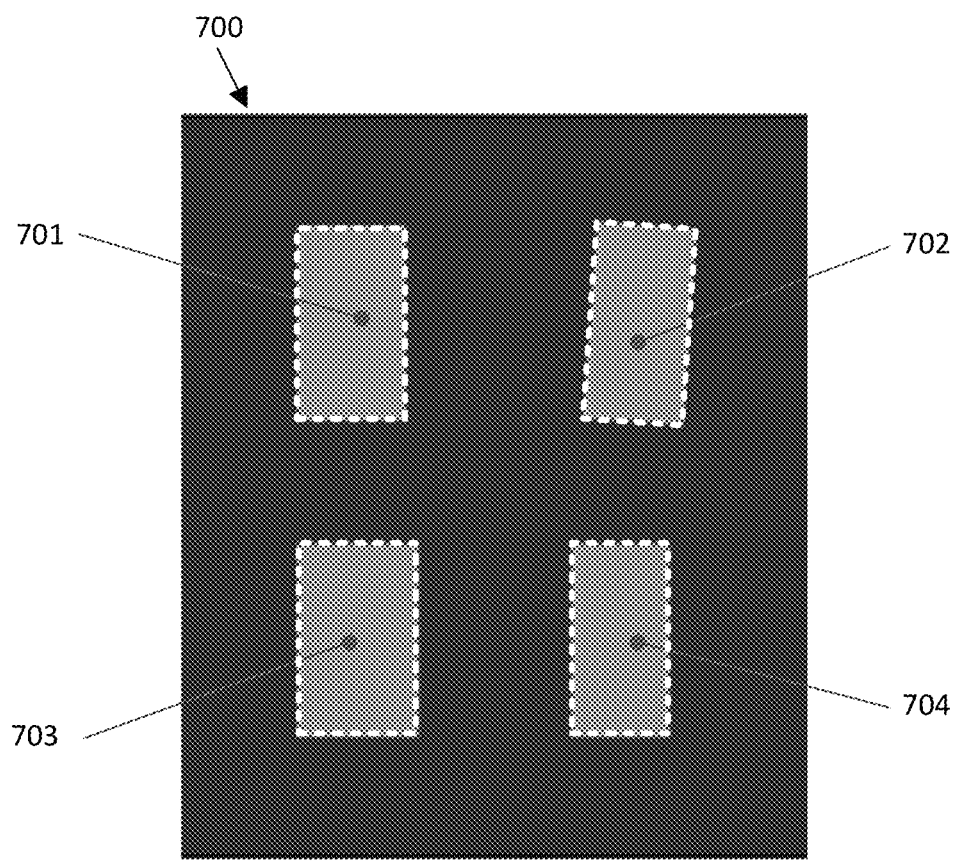
FIG. 7 illustrates care areas fitted to a die to be inspected.

FIGS. 6 and 7 illustrate an example of an implementation of ACAs according to the present disclosure wherein care areas as defined based on a die image 600 and adjusted to the features of die image 700. Die 600 contains features 601, 602, 603, and 604. Die image 700 contains features 701, 702, 703, and 704. The four ACAs are initially defined using die image 600, with each having a plurality of properties including an x-coordinate, y-coordinate, and a shape. In this embodiment, the shape of each of the four care areas is a rectangle. These ACAs are saved to a recipe, which is then used to inspect die image 700. The features of image 700 differ from the features of image 600 as follows. Feature 701 is not offset, rotated, or scaled as compared to feature 601. Feature 702 is rotated as compared to feature 602. Feature 703 has increased width as compared to feature 603. Feature 704 has undergone a shift as compared to feature 604. For each feature in die image 700, the ACA has adjusted to the relevant feature. The ACA corresponding originally to feature 601 has undergone no transformation to adjust to feature 701. The ACA corresponding originally to feature 602 has undergone rotation to adjust to feature 702. The ACA corresponding originally to feature 603 has undergone scaling to adjust to feature 703. The ACA corresponding originally to feature 604 has undergone translation to adjust to feature 704. Thus, the use of ACAs that were originally defined based on the features of die image 600 have adjusted to the features of die image 700 to permit proper inspection of the features of die image 700. This adjustment can be performed, in an instance, by detecting each corner as a salient point, determining features for each corner, parametrizing the ACA based on the features determined, setting a search window around each salient point, and finding a match to adapt the ACA to the actual feature. Further, the shape of this adapted ACA can be compared against the original ACA. In this way, the adjustment deformations of the ACAs can be quantified as the change type and amount between the features of die image 600 and die image 700. These quantified adjustment deformations can be used as defect attributes for process tracking.

Figure 8:
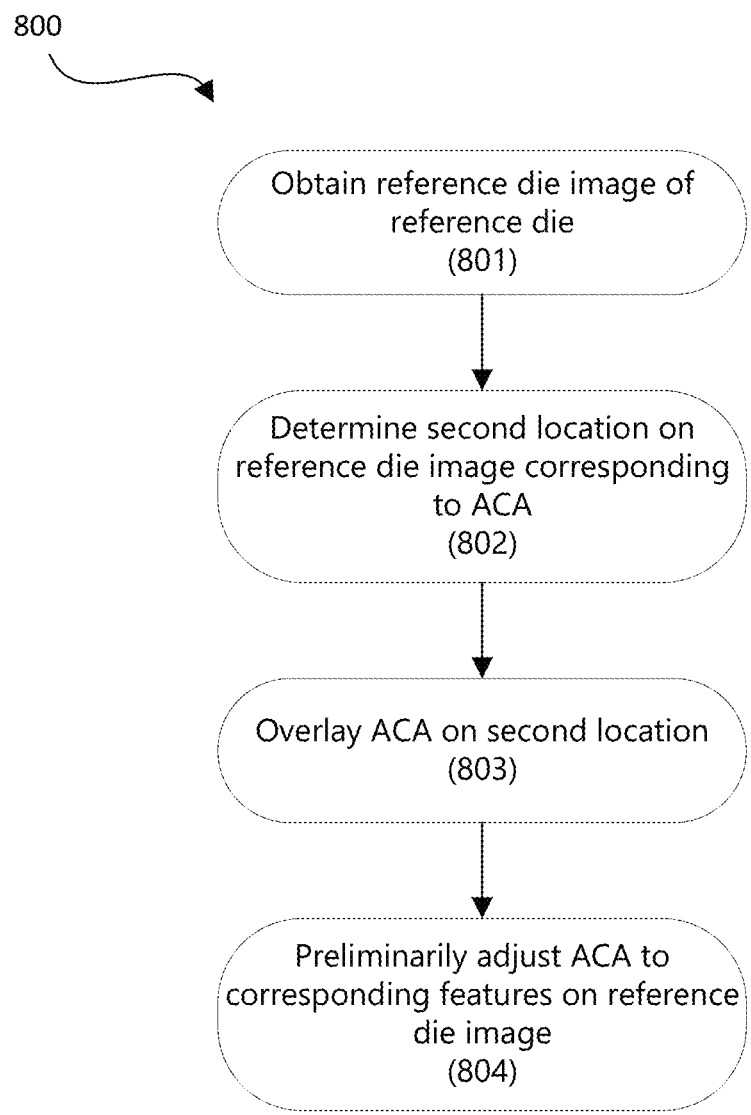
FIG. 8 illustrates a method of performing a preliminary adjustment to an adaptive care area in accordance with the present disclosure.

In some embodiments of the present disclosure, a reference die is used to perform a preliminary adjustment to an ACA either before it is saved to a recipe or after it is saved to a recipe. FIG. 8 illustrates a method 800 according to some embodiments of the present disclosure of performing such a preliminary adjustment to an ACA. Method 800 includes obtaining at 801 a reference die image. At 802, a second location corresponding to the ACA on the reference die image is determined. At 803, the ACA is overlaid on the location determined in 802. At 804, the ACA is adjusted to its corresponding features on the reference die image. This adjustment can include rotation, translation, scaling, or other transformations. The adjusted ACA resulting from 804 is then stored to the recipe and used for further inspections of test wafers.

The reference die image can be obtained from a reference die, which can be a golden die having verified features chosen by a user during recipe setup, a median of two or more neighboring dies to the die under inspected, or a design image simulated from a design file. If obtained from a physical die, the reference die image can be obtained using a tool such as using an optical microscope, a broad-beam plasma tool, or a scanning electron microscope.

According to some embodiments, a second location on the reference die image can be determined in the same manner as the first location described above.

In an embodiment of the present disclosure, methods 500 or 800 described herein are implemented on a processor.

In another embodiment of the present disclosure, the above methods are implemented as one or more programs for execution on one or more computing devices. In this embodiment, the one or more programs are stored on a non-transitory computer-readable storage medium. The computer-implemented method may include any step(s) of any method(s) described herein.

Figure 9:
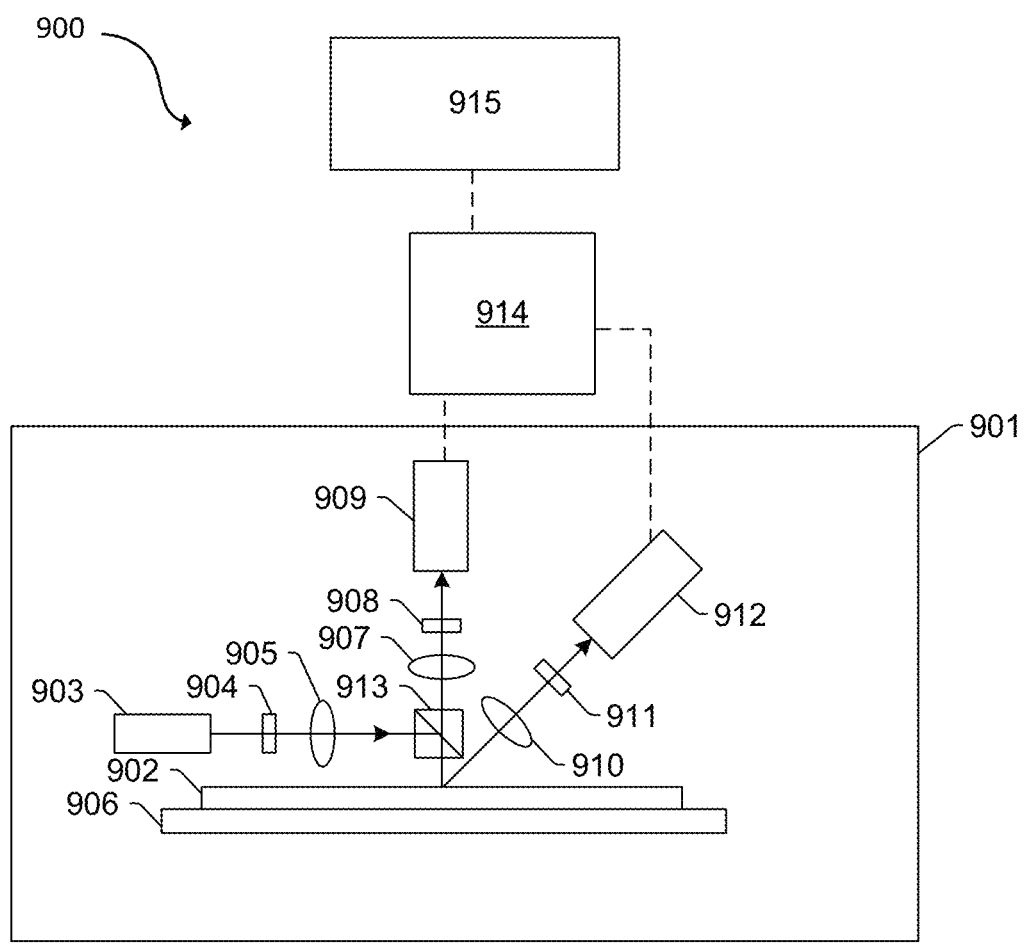
FIG. 9 illustrates a system embodiment of the present disclosure.

One embodiment of a system 900 is shown in FIG. 9. The system 900 includes optical based subsystem 901. In general, the optical based subsystem 901 is configured for generating optical based output for a specimen 902 by directing light to (or scanning light over) and detecting light from the specimen 902. In one embodiment, the specimen 902 includes a wafer. The wafer may include any wafer known in the art. In another embodiment, the specimen includes a reticle. The reticle may include any reticle known in the art.

In the embodiment of the system 900 shown in FIG. 9, optical based subsystem 901 includes an illumination subsystem configured to direct light to specimen 902. The illumination subsystem includes at least one light source (e.g., a particle emitter). For example, as shown in FIG. 9, the illumination subsystem includes light source 903. In one embodiment, the illumination subsystem is configured to direct the light to the specimen 902 at one or more angles of incidence, which may include one or more oblique angles and/or one or more normal angles. For example, as shown in FIG. 9, light from light source 903 is directed through optical element 904 and then lens 905 to specimen 902 at an oblique angle of incidence. The oblique angle of incidence may include any suitable oblique angle of incidence, which may vary depending on, for instance, characteristics of the specimen 902.

The particles emitted from the light source 903, or particle emitter, can be photons. The light source 903, or particle emitter can also emit light, which can be infrared, visible, ultraviolet, or x-ray light.

The optical based subsystem 901 may be configured to direct the light to the specimen 902 at different angles of incidence at different times. For example, the optical based subsystem 901 may be configured to alter one or more characteristics of one or more elements of the illumination subsystem such that the light can be directed to the specimen 902 at an angle of incidence that is different from that shown in FIG. 9. In one such example, the optical based subsystem 901 may be configured to move light source 903, optical element 904, and lens 905 such that the light is directed to the specimen 902 at a different oblique angle of incidence or a normal (or near normal) angle of incidence.

In some instances, the optical based subsystem 901 may be configured to direct light to the specimen 902 at more than one angle of incidence at the same time. For example, the illumination subsystem may include more than one illumination channel, one of the illumination channels may include light source 903, optical element 904, and lens 905 as shown in FIG. 9 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen 902 at different angles of incidence may be different such that light resulting from illumination of the specimen 902 at the different angles of incidence can be discriminated from each other at the detector(s).

In another instance, the illumination subsystem may include only one light source (e.g., light source 903 shown in FIG. 9) and light from the light source may be separated into different optical paths (e.g., based on wavelength, polarization, etc.) by one or more optical elements (not shown) of the illumination subsystem. Light in each of the different optical paths may then be directed to the specimen 902. Multiple illumination channels may be configured to direct light to the specimen 902 at the same time or at different times (e.g., when different illumination channels are used to sequentially illuminate the specimen). In another instance, the same illumination channel may be configured to direct light to the specimen 902 with different characteristics at different times. For example, in some instances, optical element 904 may be configured as a spectral filter and the properties of the spectral filter can be changed in a variety of different ways (e.g., by swapping out the spectral filter) such that different wavelengths of light can be directed to the specimen 902 at different times. The illumination subsystem may have any other suitable configuration known in the art for directing the light having different or the same characteristics to the specimen 902 at different or the same angles of incidence sequentially or simultaneously.

In one embodiment, light source 903 may include a broadband plasma (BBP) source. In this manner, the light generated by the light source 903 and directed to the specimen 902 may include broadband light. However, the light source may include any other suitable light source such as a laser or lamp. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source 903 may also include a polychromatic light source that generates light at multiple discrete wavelengths or wavebands.

Light from optical element 904 may be focused onto specimen 902 by lens 905. Although lens 905 is shown in FIG. 9 as a single refractive optical element, it is to be understood that, in practice, lens 905 may include a number of refractive and/or reflective optical elements that in combination focus the light from the optical element to the specimen. The illumination subsystem shown in FIG. 9 and described herein may include any other suitable optical elements (not shown). Examples of such optical elements include, but are not limited to, polarizing component(s), spectral filter(s), spatial filter(s), reflective optical element(s), apodizer(s), beam splitter(s) (such as beam splitter 913), aperture(s), and the like, which may include any such suitable optical elements known in the art. In addition, the optical based subsystem 901 may be configured to alter one or more of the elements of the illumination subsystem based on the type of illumination to be used for generating the optical based output.

The optical based subsystem 901 may also include a scanning subsystem configured to cause the light to be scanned over the specimen 902. For example, the optical based subsystem 901 may include stage 906 on which specimen 902 is disposed during optical based output generation. The scanning subsystem may include any suitable mechanical and/or robotic assembly (that includes stage 906) that can be configured to move the specimen 902 such that the light can be scanned over the specimen 902. In addition, or alternatively, the optical based subsystem 901 may be configured such that one or more optical elements of the optical based subsystem 901 perform some scanning of the light over the specimen 902. The light may be scanned over the specimen 902 in any suitable fashion such as in a serpentine-like path or in a spiral path.

The optical based subsystem 901 further includes one or more detection channels. At least one of the one or more detection channels includes a detector configured to detect light from the specimen 902 due to illumination of the specimen 902 by the subsystem and to generate output responsive to the detected light. For example, the optical based subsystem 901 shown in FIG. 9 includes two detection channels, one formed by collector 907, element 908, and detector 909 and another formed by collector 910, element 911, and detector 912. As shown in FIG. 9, the two detection channels are configured to collect and detect light at different angles of collection. In some instances, both detection channels are configured to detect scattered light, and the detection channels are configured to detect tight that is scattered at different angles from the specimen 902. However, one or more of the detection channels may be configured to detect another type of light from the specimen 902 (e.g., reflected light).

As further shown in FIG. 9, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 910, element 911, and detector 912 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 9 shows an embodiment of the optical based subsystem 901 that includes two detection channels, the optical based subsystem 901 may include a different number of detection channels (e.g., only one detection channel or two or more detection channels). In one such instance, the detection channel formed by collector 910, element 911, and detector 912 may form one side channel as described above, and the optical based subsystem 901 may include an additional detection channel (not shown) formed as another side channel that is positioned on the opposite side of the plane of incidence. Therefore, the optical based subsystem 901 may include the detection channel that includes collector 907, element 908, and detector 909 and that is centered in the plane of incidence and configured to collect and detect light at scattering angle(s) that are at or close to normal to the specimen 902 surface. This detection channel may therefore be commonly referred to as a "top" channel, and the optical based subsystem 901 may also include two or more side channels configured as described above. As such, the optical based subsystem 901 may include at least three channels (i.e., one top channel and two side channels), and each of the at least three channels has its own collector, each of which is configured to collect light at different scattering angles than each of the other collectors.

As described further above, each of the detection channels included in the optical based subsystem 901 may be configured to detect scattered light. Therefore, the optical based subsystem 901 shown in FIG. 9 may be configured for dark field (DF) output generation for specimens 902. However, the optical based subsystem 901 may also or alternatively include detection channel(s) that are configured for bright field (BF) output generation for specimens 902. In other words, the optical based subsystem 901 may include at least one detection channel that is configured to detect light specularly reflected from the specimen 902. Therefore, the optical based subsystems 901 described herein may be configured for only DF, only BF, or both DF and BF imaging. Although each of the collectors are shown in FIG. 9 as single refractive optical elements, it is to be understood that each of the collectors may include one or more refractive optical die(s) and/or one or more reflective optical element(s).

The one or more detection channels may include any suitable detectors known in the art. For example, the detectors may include photo-multiplier tubes (PMTs), charge coupled devices (CCDs), time delay integration (TDI) cameras, and any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the optical based subsystem may be signals or data, but not image signals or image data. In such instances, a processor such as processor 914 may be configured to generate images of the specimen 902 from the non-imaging output of the detectors. However, in other instances, the detectors may be configured as imaging detectors that are configured to generate imaging signals or image data. Therefore, the optical based subsystem may be configured to generate optical images or other optical based output described herein in a number of ways.

It is noted that FIG. 9 is provided herein to generally illustrate a configuration of an optical based subsystem 901 that may be included in the system embodiments described herein or that may generate optical based output that is used by the system embodiments described herein. The optical based subsystem 901 configuration described herein may be altered to optimize the performance of the optical based subsystem 901 as is normally performed when designing a commercial output acquisition system. In addition, the systems described herein may be implemented using an existing system (e.g., by adding functionality described herein to an existing system). For some such systems, the methods described herein may be provided as optional functionality of the system (e.g., in addition to other functionality of the system). Alternatively, the system described herein may be designed as a completely new system.

Figure 10:
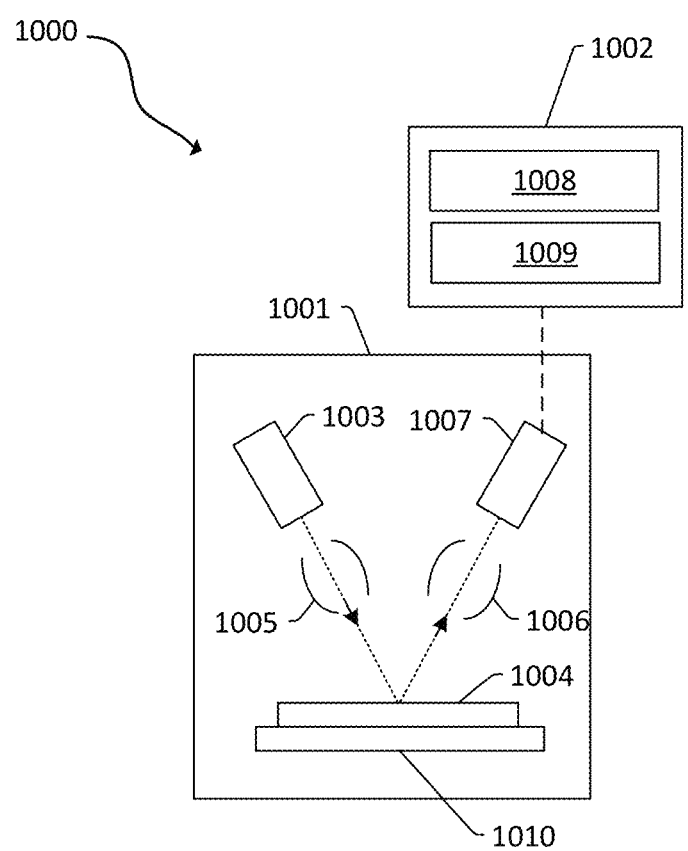
FIG. 10 illustrates another system embodiment of the present disclosure.

FIG. 10 is a block diagram of an embodiment of a system 1000. The system 1000 includes a wafer inspection tool (which includes the electron column 1001) configured to generate images of a specimen 1004, which may include a wafer or a reticle.

The wafer inspection tool includes an output acquisition subsystem that includes at least an energy source and a detector. The output acquisition subsystem may be an electron beam-based output acquisition subsystem. For example, in one embodiment, the energy directed to the specimen 1004 includes electrons, and the energy detected from the specimen 1004 includes electrons. In this manner, the energy source may be an electron beam source. In one such embodiment shown in FIG. 10, the output acquisition subsystem includes electron column 1001, which is coupled to computer subsystem 1002. A stage 1010 may hold the specimen 1004.

As also shown in FIG. 10, the electron column 1001 includes an electron beam source 1003 (e.g., a particle emitter) configured to generate electrons that are focused to specimen 1004 by one or more elements 1005. The electron beam source 1003 may include, for example, a cathode source or emitter tip. The one or more elements 1005 may include, for example, a gun lens, an anode, a beam limiting aperture, a gate valve, a beam current selection aperture, an objective lens, and a scanning subsystem, all of which may include any such suitable elements known in the art.

Electrons returned from the specimen 1004 (e.g., secondary electrons) may be focused by one or more elements 1006 to detector 1007. One or more elements 1006 may include, for example, a scanning subsystem, which may be the same scanning subsystem included in element(s) 1005.

The electron column 1001 also may include any other suitable elements known in the art.

Although the electron column 1001 is shown in FIG. 10 as being configured such that the electrons are directed to the specimen 1004 at an oblique angle of incidence and are scattered from the specimen 1004 at another oblique angle, the electron beam may be directed to and scattered from the specimen 1004 at any suitable angles. In addition, the electron beam-based output acquisition subsystem may be configured to use multiple modes to generate images of the specimen 1004 (e.g., with different illumination angles, collection angles, etc.). The multiple modes of the electron beam-based output acquisition subsystem may be different in any image generation parameters of the output acquisition subsystem.

Computer subsystem 1002 may be coupled to detector 1007 as described above. The detector 1007 may detect electrons returned from the surface of the specimen 1004 thereby forming electron beam images of the specimen 1004. The electron beam images may include any suitable electron beam images. Computer subsystem 1002 may be configured to perform any of the functions described herein using the output of the detector 1007 and/or the electron beam images. Computer subsystem 1002 may be configured to perform any additional step(s) described herein. A system 1000 that includes the output acquisition subsystem shown in FIG. 10 may be further configured as described herein.

It is noted that FIG. 10 is provided herein to generally illustrate a configuration of an electron beam-based output acquisition subsystem that may be used in the embodiments described herein. The electron beam-based output acquisition subsystem configuration described herein may be altered to optimize the performance of the output acquisition subsystem as is normally performed when designing a commercial output acquisition system. In addition, the systems described herein may be implemented using an existing system (e.g., by adding functionality described herein to an existing system). For some such systems, the methods described herein may be provided as optional functionality of the system (e.g., in addition to other functionality of the system). Alternatively, the system described herein may be designed as a completely new system.

Although the output acquisition subsystem is described above as being an electron beam-based output acquisition subsystem, the output acquisition subsystem may be an ion beam-based output acquisition subsystem. Such an output acquisition subsystem may be configured as shown in FIG. 10 except that the electron beam source may be replaced with any suitable ion beam source known in the art. In addition, the output acquisition subsystem may be any other suitable ion beam-based output acquisition subsystem such as those included in commercially available focused ion beam (FIB) systems, helium ion microscopy (HIM) systems, and secondary ion mass spectroscopy (SIMS) systems.

The computer subsystem 1002 includes a processor 1008 and an electronic data storage unit 1009. The processor 1008 may include a microprocessor, a microcontroller, or other devices.

The processor 914 or computer subsystem 1002 may be coupled to the components of the system 900 or 1000, respectively, in any suitable manner (e.g., via one or more transmission media, which may include wired and/or wireless transmission media) such that the processor 914 or 1008, respectively can receive output. The processor 914 or 1008 may be configured to perform a number of functions using the output. The system 900 or 1000 can receive instructions or other information from the processor 914 or 1008, respectively. The processor 914 or 1008 and/or the electronic data storage unit 915 or 1009, respectively, optionally may be in electronic communication with another wafer inspection tool, a wafer metrology tool, or a wafer review tool (not illustrated) to receive additional information or send instructions. For example, the processor 914 or 1008 and/or the electronic data storage unit 915 or 1009, respectively, can be in electronic communication with a scanning electron microscope.

The processor 914 or 1008, or computer subsystem 1002, other system(s), or other subsystem(s) described herein may be part of various systems, including a personal computer system, image computer, mainframe computer system, workstation, network appliance, internet appliance, or other device. The subsystem(s) or system(s) may also include any suitable processor known in the art, such as a parallel processor. In addition, the subsystem(s) or system(s) may include a platform with high-speed processing and software, either as a standalone or a networked tool.

The processor 914 or 1008 and electronic data storage unit 915 or 1009, respectively, may be disposed in or otherwise part of the system 900 or 1000, respectively, or another device. In an example, the processor 914 or 1008 and electronic data storage unit 915 or 1009, respectively may be part of a standalone control unit or in a centralized quality control unit. Multiple processors 914 or 1008 or electronic data storage units 915 or 1009, respectively, may be used.

The processor 914 or 1008 may be implemented in practice by any combination of hardware, software, and firmware. Also, its functions as described herein may be performed by one unit, or divided up among different components, each of which may be implemented in turn by any combination of hardware, software and firmware. Program code or instructions for the processor 914 or 1008 to implement various methods and functions may be stored in readable storage media, such as a memory in the electronic data storage unit 915 or 1009, respectively, or other memory.

If the system 900 or 1000 includes more than one processor 914, or processor 1008 or computer subsystem 1002, respectively, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 914 or 1008 may be configured to perform a number of functions using the output of the system 900 or 1000, respectively, or other output. For instance, the processor 914 or 1008 may be configured to send the output to an electronic data storage unit 915 or 1009, respectively, or another storage medium. The processor 914 or 1008 may be further configured as described herein.

The processor 914, processor 1008, or computer subsystem 1002 may be part of a defect review system, an inspection system, a metrology system, or some other type of system. Thus, the embodiments disclosed herein describe some configurations that can be tailored in a number of manners for systems having different capabilities that are more or less suitable for different applications.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

The processor 914 or 1008 may be configured according to any of the embodiments described herein. The processor 914 or 1008 also may be configured to perform other functions or additional steps using the output of the system 900 or 1000, respectively, or using images or data from other sources.

The processor 914 or 1008 may be communicatively coupled to any of the various components or sub-systems of system 900 or 1000, respectively, in any manner known in the art. Moreover, the processor 914 or 1008 may be configured to receive and/or acquire data or information from other systems (e.g., inspection results from an inspection system such as a review tool, a remote database including design data and the like) by a transmission medium that may include wired and/or wireless portions. In this manner, the transmission medium may serve as a data link between the processor 914 or 1008 and other subsystems of the system 900 or 1000, respectively, or systems external to system 900 or 1000, respectively.

The processor 914 or 1008 is in electronic communication with the wafer inspection tool, such as the detector 909 or 912, or detector 1007, respectively. The processor 914 or 1008 may be configured to process images generated using measurements from the detector 909 or 912, or detector 1007, respectively. For example, the processor 914 or 1008 may be configured to perform embodiments of the methods 500 or 800.

An additional embodiment relates to a non-transitory computer-readable medium storing program instructions executable on a controller for performing a computer-implemented method for processing images of the specimen 902 or 1004, as disclosed herein. In particular, as shown in FIG. 9 or 10, electronic data storage unit 915 or 1009, or other storage medium may contain non-transitory computer-readable medium that includes program instructions executable on the processor 914 or 1008, respectively. The computer-implemented method may include any step(s) of any method (s) described herein, including methods 500 or 800.

Program instructions implementing methods such as those described herein may be stored on computer-readable medium, such as in the electronic data storage unit 915 or 1009, or other storage medium. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), Streaming SIMD Extension (SSE), or other technologies or methodologies, as desired.

In an embodiment, processor 914 or processor 1008 may be configured to: receive a die image from the inspection tool 900 or inspection tool 1000; read a recipe containing an ACA, the ACA having a plurality of pre-determined properties comprising an x-coordinate, a y-coordinate, and a shape; and for each ACA, determine a first location on the die image corresponding to the ACA, overlay the ACA on the first location on the die image; adjust the ACA to one or more corresponding elements on the die image; and perform a defect inspection of the die image within the ACA.

In an embodiment, the processor 914 or processor 1008 may be further configured to: receive a reference die image from an inspection tool; read a recipe containing an ACA, the ACA having a plurality of pre-determined properties comprising an x-coordinate, a y-coordinate, and a shape; determine a second location on the reference die image corresponding to the ACA; overlay the ACA on the second location on the reference die image, and preliminarily adjust the ACA to one or more corresponding features on the reference die image.

In an embodiment, the processor 914 or processor 1008 may be further configured to read an ACA wherein the ACA comprises a shape that is either a polygon, ellipse, or user-defined irregular shape.

Various steps, functions, and/or operations of system 900 or system 1000 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape, and the like. A carrier medium may include a transmission medium such as a wire, cable, or wireless transmission link. For instance, the various steps described throughout the present disclosure may be carried out by a single processor 914 or a single processor 1008 (or computer subsystem 1002) or, alternatively, multiple processors 914 or multiple processors 1008 (or multiple computer subsystems 1002). Moreover, different sub-systems of the system 900 or system 1000 may include one or more computing or logic systems.

Therefore, the above description should not be interpreted as a limitation on the present disclosure but merely an illustration.

In some embodiments, in obtaining a die image of a wafer 503, the die image of a wafer is a simulated image obtained from a design file. The ACAs are overlaid on this simulated image. Feature matching is performed as described herein, the ACAs are adapted, and inspection is performed.

In some embodiments, in obtaining a die image of a wafer 503, the die image of a wafer is a design file. The ACAs are overlaid on the design file. Feature matching is performed as described herein, the ACAs are adapted, and inspection is performed.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

Although the present disclosure has been described with respect to one or more particular embodiments and/or examples, it will be understood that other embodiments and/or examples of the present disclosure may be made without departing from the scope of the present disclosure.

What is claimed is:

1. A method of performing a defect inspection, comprising:
   defining at least a first adaptive care area and a second adaptive care area, each of the adaptive care areas having a plurality of pre-determined properties comprising:
   an x-coordinate;
   a y-coordinate; and
   a shape;
   saving the adaptive care areas to a recipe, wherein the recipe is stored within an electronic data storage unit that contains a non-transitory computer-readable medium;
   obtaining a die image of a wafer on a stage using an inspection tool comprising a particle emitter and a detector; and
   at a processor, reading the recipe from the electronic data storage unit, and using the processor for the adaptive care areas saved in the recipe by:
   determining a first location on the die image corresponding to the first adaptive care area;
   overlaying the first adaptive care area on the first location on the die image;
   adjusting the first adaptive care area to one or more corresponding features on the die image, wherein the second adaptive care area is fixed relative to the first location on the die image during the adjusting; and
   performing a defect inspection of the die image within the first adaptive care area.

2. The method of claim 1, wherein the particle emitter includes a broadband plasma source, electron beam source, lamp, or laser.

3. The method of claim 1, wherein the shape is a polygon or an ellipse.

4. The method of claim 1, wherein the shape is a user-defined irregular shape.

5. The method according to claim 1, wherein the plurality of pre-determined properties further comprises at least one feature property.

6. The method of claim 5, wherein the feature property comprises: a scaled invariant feature transform, a speeded-up robust feature, an oriented rotated brief, a histogram of oriented gradients, a corner-detector, or a gradient-based descriptor.

7. The method of claim 1, wherein adjusting the first adaptive care area to one or more corresponding features on the die image comprises one or more of: translation, rotation, scaling, affine transformation, perspective warping, or projective distortion.

8. The method of claim 1, further comprising determining one or more adjustment limits, wherein adjusting the first adaptive care area to the one or more corresponding features in the die image is constrained by the one or more adjustment limits.

9. The method of claim 1, wherein the shape is a polygon, and wherein adjusting the first adaptive care area to the one or more corresponding features on the die image comprises adjusting at least one corner of the polygon.

10. The method of claim 9, further comprising determining one or more adjustment limits, wherein adjusting the corner of the polygon is constrained by the one or more adjustment limits.

11. The method of claim 1, further comprising performing a preliminary adjustment to the first adaptive care area prior to using the inspection tool to obtain the die image, the preliminary adjustment to the adaptive care area comprising:
obtaining a reference die image of a reference die, wherein the reference die is a golden die having verified features, a synthetic die calculated from the median of neighboring dies, or a design image simulated from a design file; and
at the processor, reading the recipe from the electronic data storage unit, and using the processor for the adaptive care area saved in the recipe by:
determining a second location on the reference die image corresponding to the first adaptive care area,
overlaying the first adaptive care area on the second location on the reference die image, and
preliminarily adjusting the first adaptive care area to one or more corresponding elements on the reference die image.

12. A defect inspection system, comprising:
an inspection tool comprising:
a particle emitter configured to emit particles in a particle beam,
a stage configured to hold a wafer in a path of the particle beam emitted by the particle emitter, and
a detector configured to detect a portion of the particles reflected by the wafer and yield a die image;
an electronic data storage unit that contains a non-transitory computer-readable medium configured to store a recipe, the recipe comprising at least a first adaptive care area and a second adaptive care area, each of the adaptive care area having a plurality of pre-determined properties comprising:
an x-coordinate,
a y-coordinate, and
a shape; and
a processor in electronic communication with the inspection tool and the electronic data storage unit configured to:
receive the die image from the inspection tool;
read the recipe from the electronic data storage unit, and for the first adaptive care area saved in the recipe:
determine a first location on the die image corresponding to the first adaptive care area,
overlay the first adaptive care area on the first location on the die image;
adjust the first adaptive care area to one or more corresponding elements on the die image, wherein the second adaptive care area is fixed relative to the first location on the die image during the adjusting; and
perform a defect inspection of the die image within the first adaptive care area.

13. The system of claim 12, wherein the processor is further configured to read the recipe from the electronic data storage unit, and for the first adaptive care area saved in the recipe:
determine a second location on a reference die image corresponding to the first adaptive care area, wherein the reference die image is obtained from a golden die having verified features, a synthetic die calculated from the median of neighboring dies, or a design image simulated from a design file;
overlay the first adaptive care area on the second location on the reference die image; and
preliminarily adjust the first adaptive care area to one or more corresponding features on the reference die image.

14. The system of claim 12, wherein the particles are photons or electrons.

15. The system of claim 12, wherein the shape is a polygon or an ellipse.

16. The system of claim 12, wherein the shape is a user-defined irregular shape.

17. A non-transitory computer-readable storage medium, comprising one or more programs for executing the following steps on one or more computing devices:
define a first adaptive care area and a second adaptive care area, each of the adaptive care areas having a plurality of pre-determined properties comprising:
an x-coordinate;
a y-coordinate; and
a shape;
save the adaptive care areas to a recipe;
obtain, from an inspection tool comprising a particle emitter and a detector, a die image of a wafer on a stage; and
read the recipe, and for the first adaptive care area saved in the recipe:
determine a location on the die image corresponding to the first adaptive care area;
overlay the first adaptive care area on the location on the die image;
adjust the first adaptive care area to one or more corresponding features on the die image, wherein the second adaptive care area is fixed relative to the location on the die image during the adjusting; and
send instructions to perform a defect inspection of the die image within the first adaptive care area.

18. The non-transitory computer-readable storage medium of claim 17, wherein the shape is a polygon or an ellipse.

19. The non-transitory computer-readable storage medium of claim 17, wherein the shape is a user-defined irregular shape.

20. The non-transitory computer-readable storage medium of claim 17, wherein one or more adjustment limits are determined, wherein adjusting the first adaptive care area to one or more corresponding features in the die image is constrained by the one or more adjustment limits.

\* \* \* \* \*